(12) United States Patent
Karmali

(10) Patent No.: US 8,802,831 B2
(45) Date of Patent: *Aug. 12, 2014

US008802831B2

(54) COMPOSITIONS AND METHODS OF IMPROVING THE TOLERABILITY OF DAUNORUBICIN WHEN GIVEN AS OROTATE SALT

(75) Inventor: Rashida A. Karmali, Brooklyn, NY (US)

(73) Assignee: Savvipharm Inc, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/385,638

(22) Filed: Feb. 27, 2012

(65) Prior Publication Data

US 2012/0202761 A1 Aug. 9, 2012

Related U.S. Application Data

(60) Continuation-in-part of application No. 12/316,548, filed on Dec. 12, 2008, now Pat. No. 8,148,339, which is a division of application No. 11/496,255, filed on Jul. 31, 2006, now Pat. No. 7,470,672.

(51) Int. Cl.
| | | |
|---|---|---|
| *C07H 15/252* | (2006.01) | |
| *C07D 239/557* | (2006.01) | |
| *A61K 38/12* | (2006.01) | |
| *A61K 38/20* | (2006.01) | |
| *A61K 31/704* | (2006.01) | |
| *A61K 31/513* | (2006.01) | |

(52) U.S. Cl.
CPC ............ *C07H 15/252* (2013.01); *A61K 38/12* (2013.01); *A61K 38/2013* (2013.01); *A61K 31/704* (2013.01); *A61K 31/513* (2013.01)

USPC ............................................. 536/6.4; 514/34

(58) Field of Classification Search
CPC ........................ C07D 239/557; C07H 15/252
See application file for complete search history.

(56) References Cited

U.S. PATENT DOCUMENTS

| | | | |
|---|---|---|---|
| 5,304,687 A | | 4/1994 | Bargiotti et al. |
| 5,391,723 A | * | 2/1995 | Priest ........................... 536/23.1 |
| 5,605,703 A | | 2/1997 | Lambiez et al. |
| 6,210,930 B1 | | 4/2001 | Filippini et al. |
| 6,284,737 B1 | | 9/2001 | Farquhar et al. |
| 6,653,455 B1 | | 11/2003 | Johdo et al. |

FOREIGN PATENT DOCUMENTS

EP 0840608 B1 * 10/2004 ......... A61K 31/4192

OTHER PUBLICATIONS

Merriam-Webster: Composition definition; http://www.merriam-webster.com/dictionary/composition, accessed Jun. 12, 2013.*
Gabizon et al Cancer Research 1998, 52: 891-896.
Van Hossel et al Cancer Res 1984, 44:3698-3705.

* cited by examiner

*Primary Examiner* — Timothy Thomas
(74) *Attorney, Agent, or Firm* — Rashida A. Karmali

(57) ABSTRACT

This invention is in the field of anthracycline family of drugs. More particularly, it concerns converting daunorubicin hydrochloride to an orotate salt and providing methods of improving the tolerability of daunorubicin in animals by reducing the adverse effects and toxicity in noncancerous tissues. Daunorubicin orotate provides a safer treatment for specific types of leukemias and neuroblastomas in adults and in pediatric patients.

2 Claims, 4 Drawing Sheets

COMPOSITIONS AND METHODS OF IMPROVING THE TOLERABILITY OF DAUNORUBICIN WHEN GIVEN AS OROTATE SALT

CROSS-REFERENCE TO OTHER APPLICATION

This application is a Continuation-in-part of U.S. patent application Ser. No. 12/316,548 filed Dec. 12, 2008 now U.S. Pat. No. 8,148,339, which is a Divisional of U.S. patent application Ser. No. 11/496,255 filed on Jul. 31, 2006, issued as U.S. Pat. No. 7,470,672, issued Dec. 30, 2008 which are incorporated herein, with references.

FIELD OF INVENTION

This invention is in the field of anthracycline family of drugs. More particularly, it concerns the improved tolerability of the orotate salt of daunorubicin, that is given as treatment for specific types of leukemias and neuroblastomas in adults and in pediatric patients, by reducing the adverse effects and toxicity in noncancerous tissues.

1. BACKGROUND TO THE INVENTION

This invention is in the field of improving the tolerability of daunorubicin and reducing the toxicity or adverse drug reactions in noncancerous tissues by producing the orotate salt of daunorubicin. Daunorubicin hydrochloride (cerubidine) is a hydrochloride salt of an anthracycline antibiotic produced by a strain of *Streptomyses coeruleorubidus*. It is provided as a sterile reddish lyophilized powder in vials for intravenous administration only. It was initially isolated from *Streptomyces peucetius*. A liposomal formulation of daunorubicin is marketed as DaunoXome. Daunorubicin hydrochloride slows or stops the growth of cancer cells in the body. It is most commonly used in pediatric and adult patients to treat specific types of leukemias, for example acute myeloid leukemia and lymphocytic leukemia. Treatment is usually performed together with other chemotherapy drugs such as cytarabine, and its administration depends on the type of tumor and the degree of response. Because of its use in pediatric patients it is very important to monitor the serious toxicities associated with daunorubicin hydrochloride. Daunorubicin hydrochloride is also used as the starting material for semi-synthetic manufacturing of doxorubicin, epirubicin and idarubicin.

Mode of Action—daunorubicin binds to DNA and intercalates, with its daunosamine residue directed toward the minor groove. It has the highest preference for two adjacent G/C base pairs flanked on the 5' side chain by an ATT base pair. Daunomycin effectively binds to every 3 base pair and induces a local unwinding angle of 11° but negligible distortion of the helical conformation.

Route of Administration—daunorubicin should be administered in a rapid infusion. It should not be administered intramuscularly or subcutaneously since it may cause extensive tissue necrosis. It should never be administered intrathecally (into the spinal cord) as this will cause extensive damage to the nervous system and may lead to death. Mortensen M E et al, 1992, Med Pediatric Oncol 20: 249-253. It has been established that the use of liposomes for the administration of anti-neoplastics in many cases improves the traditional methods of administration. Gabizon, Cancer Res. (1992), 52; 891-896 and Van Hossel et al, Cancer Res (1984) 44; 3698-3705. Different patents describe the inclusion of anti-free radical agents into liposomes having improved activity as inhibitors of lipid peroxidation. U.S. Pat. No. 5,605,703, issued Feb. 25, 1997. Liposomal encapsulation can substantially affect a drug's functional properties relative to those of the unencapsulated drug. In addition, different liposomal drug products may vary from one another in the chemical composition and physical form of liposomes. Such differences can substantially affect the functional properties of liposomal drug products. A liposomal formulation is marketed in the United States as DaunoXome.

Cardiac Toxicity—The cardiac toxicity exhibited by daunorubicin hydrochloride and the other anthracyclines is unique in terms of its pathology and mechanism. The major limiting facts in the clinical use of anthracylclines in adults are bone marrow suppression, mucositis, and drug resistance on the part of the tumor. Myocardial toxicity manifests in its most severe form by potentially fatal congestive heart failure and may occur either during therapy or months to years after termination of therapy. Children seem to be more sensitive to the cardiac toxicity of this drug, and this has become a significant problem in the use of daunorubicin in pediatric oncology. Management of Drug Toxicity, Ch 31-42, in The Chemotherapy Source Book, $3^{rd}$ ed, Michael C. Perry, Lippincott Williams & Wilkins, 2001.

Thus there is a great need for analogues which give a better rate of response, a wider spectrum of response, and/or reduce cardiotoxicity. Much of the history and prior art of adriamycines are found in issued patents and published literature. U.S. Pat. No. 5,304,687 issued Apr. 19, 1994; U.S. Pat. No. 5,605,703 issued Feb. 25, 1997; U.S. Pat. No. 6,210,930 issued Apr. 3, 2001; U.S. Pat. No. 6,284,737 issued Sep. 4, 2001; and U.S. Pat. No. 6,653,455 issued Nov. 25, 2003.

However, the present invention is distinguishable from the prior art because none of the prior art addresses the issue of reducing the toxicity and adverse drug reactions in normal animals. More tolerable and less toxic agents are widely sought and are a fundamental object of the invention. The pertinent subject matter of the above references is specifically incorporated herein by reference.

3. SUMMARY OF THE INVENTION

The present invention seeks to overcome drawbacks inherent in the prior art by providing compositions of daunorubicin orotate that display increased tolerability in animals compared with daunorubicin hydrochloride as measured by change in body weight to measure the maximum tolerated dose (MTD). The MTD is defined as the dose where the drug induces a 20% loss in body weight or at least one death in the treated animal.

In view of the foregoing state of the art, the inventor has designed orotate derivatives of anthracyclines, as exemplified by daunorubicin orotate, that reduce the severity of potentially fatal toxicities observed with daunorubicin hydrochloride.

A principle objective of the invention is to obtain a composition of daunorubicin orotate in order to reduce the toxicity of the drug daunorubicin, which is related to impaired cardiac, hepatic and renal function, myelosuppression and hemorrhagic conditions which are even more grave in pediatric patients. The invention provides daunorubicin orotate that demonstrates improved tolerability in animals and will fulfill an unmet need especially in pediatric patients for whom few alternative drugs work.

The invention also specifically provides a process for the preparation of daunorubicin orotate and related derivatives starting from daunorubicin hydrochloride and orotic acid.

Another objective of the invention is to provide a method for treating human neoplasms, and particularly, primary or metastatic tumors, proliferative hematopoietic disorders and leukemias with daunorubicin orotate and reducing the toxic secondary effects of the drug and improving the tolerability when given to animals when compared with giving daunorubicin HCl.

4. BRIEF DESCRIPTION OF FIGURES

5. DETAILED DESCRIPTION OF THE INVENTION

Figure 1:
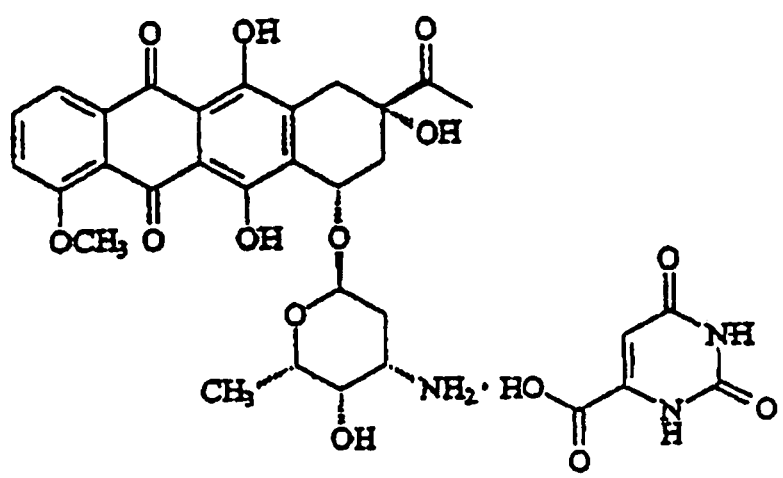
FIG. 1 illustrates the structure of daunorubicin orotate.

Drug therapies that are used for the treatment of patients with cancer can damage a number of organs and organ systems. Among those most frequently damaged are tissues with rapid cell turnover, such as the hematopoetic system, the gastrointestinal tract, and the genitourinary tract the effects are even more damaging in pediatric patients. Yet the drugs continue to be used because safer alternatives are not available.

Daunorubicin has antimitotic and cytotoxic activity through a number of proposed mechanisms of action. Daunorubicin forms complexes with DNA by intercalation between base pairs. It inhibits topoisomerase II activity by stabilizing the DNA topoisomerase II complex, prevents the relegation portion of the ligation-religation reaction that topoisomerase II catalyzes. Single strand and double strand DNA breaks result. Daunorubicin also inhibits polymerase activity, affects regulation of gene expression and produces free radical damage to DNA. Daunorubicin used as its hydrochloride salt showed antitumor effects against a wide spectrum of animal tumors as well. However, it has not been developed for clinical use in these tumors because of its serious toxicity profile.

The warning label on the injection form of daunorubicin hydrochloride reads as follows:
1. Daunorubicin Hydrochloride Injection must be given into a rapidly flowing infusion. It must never be given by the intramuscular or subcutaneous route. Severe local tissue necrosis will occur if there is extravasation during administration.
2. Myocardial toxicity manifested in its most severe form by potentially fatal congestive heart failure may occur either during therapy or months to years after termination of therapy. The incidence of myocardial toxicity increases after a total cumulative dose exceeding 400 to 550 mg/m2 in adults, 300 mg/m2 in children more than 2 years of age, or 10 mg/kg in children less than 2 years of age.
3. Severe myelosuppression occurs when used in therapeutic doses; this may lead to infection or hemorrhage.
4. It is recommended that daunorubicin hydrochloride be administered only by physicians who are experienced in leukemia chemotherapy and in facilities with laboratory and supportive resources adequate to monitor drug tolerance and protect and maintain a patient compromised by drug toxicity, hemorrhagic conditions and/or overwhelming infection.
5. Dosage should be reduced in patients with impaired hepatic or renal function.

Pharmacokinetics—Following intravenous injection of daunorubicin hydrochloride, plasma levels of daunorubicin decline rapidly indicating rapid tissue uptake and concentration. Thereafter, plasma levels decline slowly with a half-life of 45 minutes in the initial phase and 18.5 hours in the terminal phase. By 1 hour after drug administration, the predominant plasma species is Daunorubicinol, an active metabolite, which disappears with a half-life of 26.7 hours. Twenty five percent of an administered dose of daunorubicin hydrochloride in man is eliminated in an active form by urinary excretion and about 40% by biliary excretion. Therefore, doses of daunorubicin hydrochloride should be reduced in patients with hepatic and renal impairment.

Special Populations:

Pediatric Patients—Cardiotoxicity is more frequent and may occur at lower cumulative doses of daunorubicin hydrochloride in children compared to adults. Therefore, there is great need for daunorubicin orotate which is better tolerated in animals than daunorubicin hydrochloride especially for pediatric patients.

Geriatric Patients—Cardiotoxicity is more frequent in geriatric population and caution should be used in patients with inadequate bone marrow reserves due to old age. Elderly patients are more likely to have renal function impairment and may require dose reduction of daunorubicin hydrochloride. Therefore, elderly patients will benefit from daunorubicin orotate which is better tolerated in animals as shown by the maximum tolerated dose.

Maximum Tolerated Dose is defined as the dose which does not result in death or produces no more than 20% mean body weight loss.

Orotic acid, a free pyrimidine is important in the synthesis of uridylate (UPP) a major pyrimidine nucleotide. Pyrimidines play a central role in cellular regulation and metabolism. They are substrates for DNA/RNA biosynthesis, regulators of the biosynthesis of some amino acids, and cofactors in the biosynthesis of phospholipids, glycolipids, sugars and polysaccharides. The classical de novo pyrimidine biosynthetic pathway ends with the sysnthesis of UMP. Biochemistry, ed Lubert Stryer, ed, W.H. Freeman & Co NY, $4^{th}$ ed, 739-762 (1995). It has also been reported that 5-Fluorouracil is toxic to the liver, as measured by incorporation in the acid soluble fraction, RNA and DNA in normal tissues in the liver of rats. Orotic acid administration decreased the incorporation into the liver and intestinal RNA, thus suggesting that it reduces 5-FU induced toxicity in the liver. El Hag IA et al, In vivo 1: 309-312 (1987). The present invention provides drug orotate derivatives that under go dissolution to release the drug as a charged molecule and free orotic acid, which in turn reduces drug-induced liver, heart or other tissue toxicity.

The invention provides compositions of daunorubicin orotate to improve the tolerability of daunorubicin and increase effectiveness and quality of life of pediatric, geriatric and adult patients.

6. EXAMPLES

Example 1

Chemical Synthesis of Daunorubicin Orotate

Figure 2:
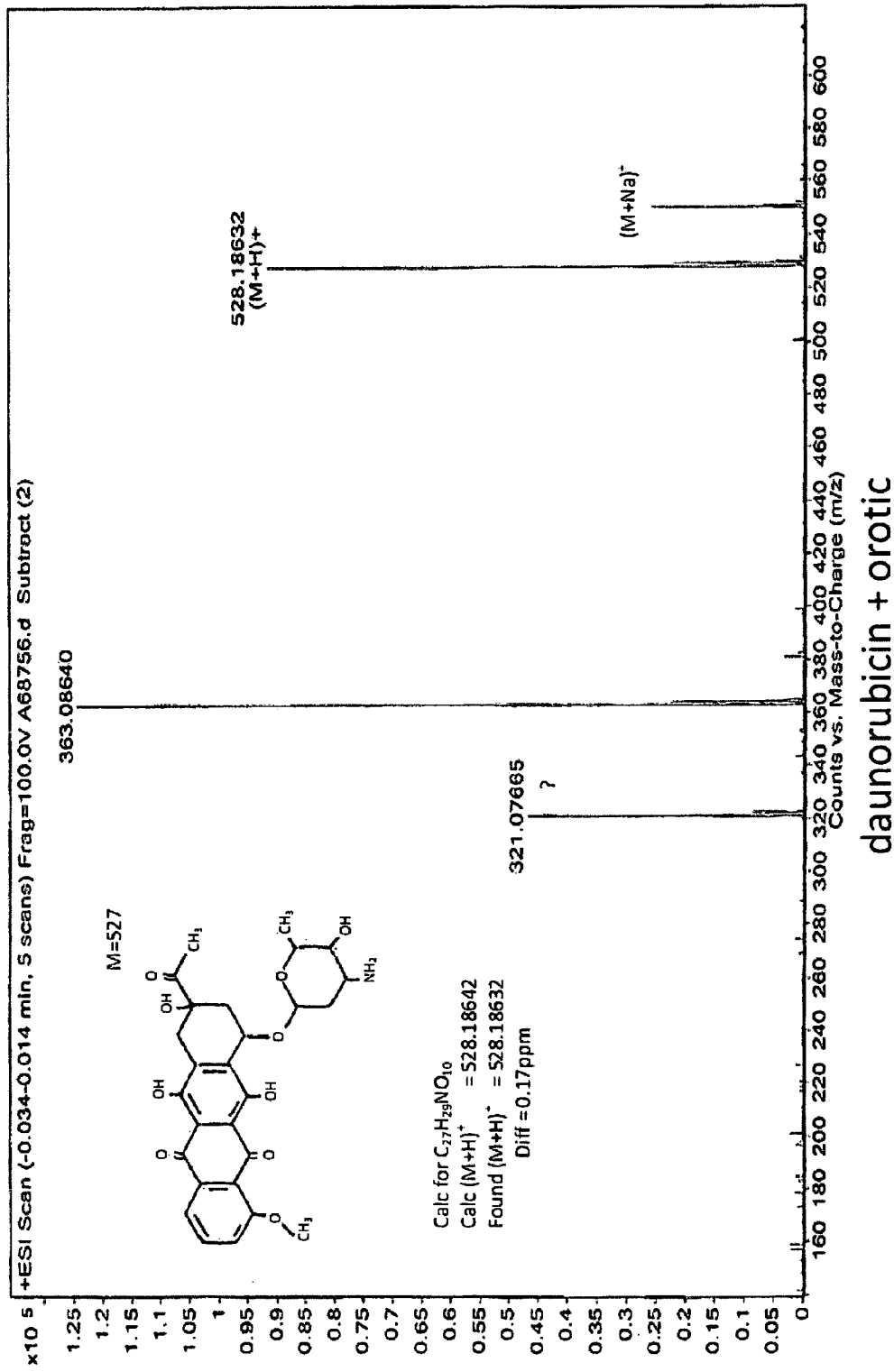
FIG. 2 illustrates the Mass Spectrograph of daunorubicin orotate.
Figure 3:
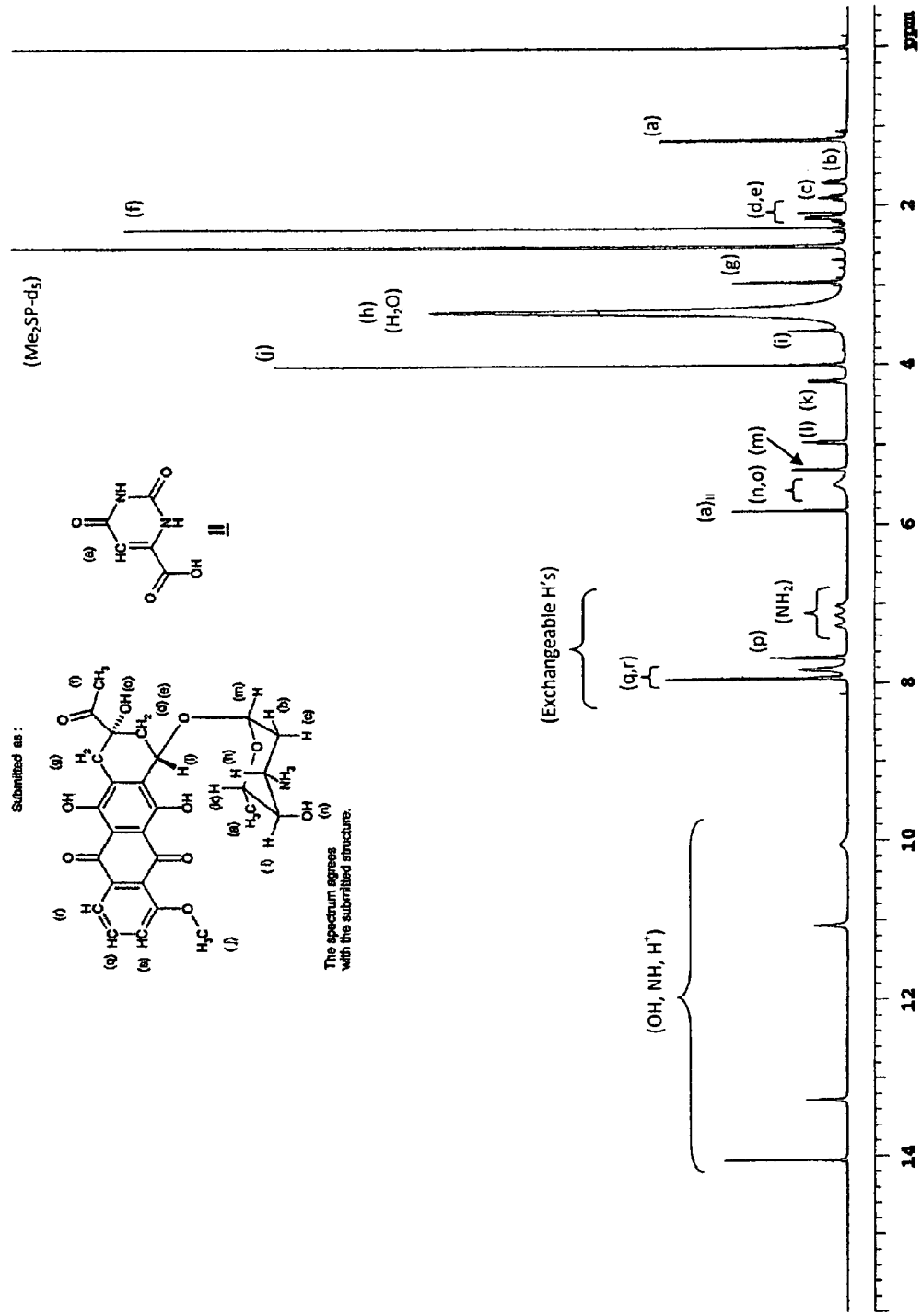
FIG. 3 illustrates the NMR of daunorubicin orotate.

FIG. 1 illustrates the synthesis of Daunorubicin Orotate. Daunorubicin hydrochloride (1.977 g, 3.80 mmole) in 150 mL of ethanol was stirred at 70° C. To the mixture ammonia in methanol (0.55 ml, 7.0N, 0.39 mmole) was added and the solution was stirred at 60° C. for 5 min. The solvent and extra ammonia were removed using a rotovapor. The residue was dissolved in the 150 mL of ethanol again. To the solution was added orotic acid monohydrate (662 mg, 0.38 mmole) and the mixture was stirred for another 30 mins. The solution was concentrated to 50 mL, stored in freezer at −20° C. overnight. The precipitate was collected by filtration, washed with 3 ml of water, 20 mL of acetone and 50 mL of ether, dried in vacuum at room temperature for 8 hours to give daunorubicin orotate as a red solid (2.24 g, 90.1%). MW=527. The structure was confirmed by Mass Spectroscopy (FIG. 2) and Nuclear Magnetic Resonance (FIG. 3).

Example 2

Figure 4:
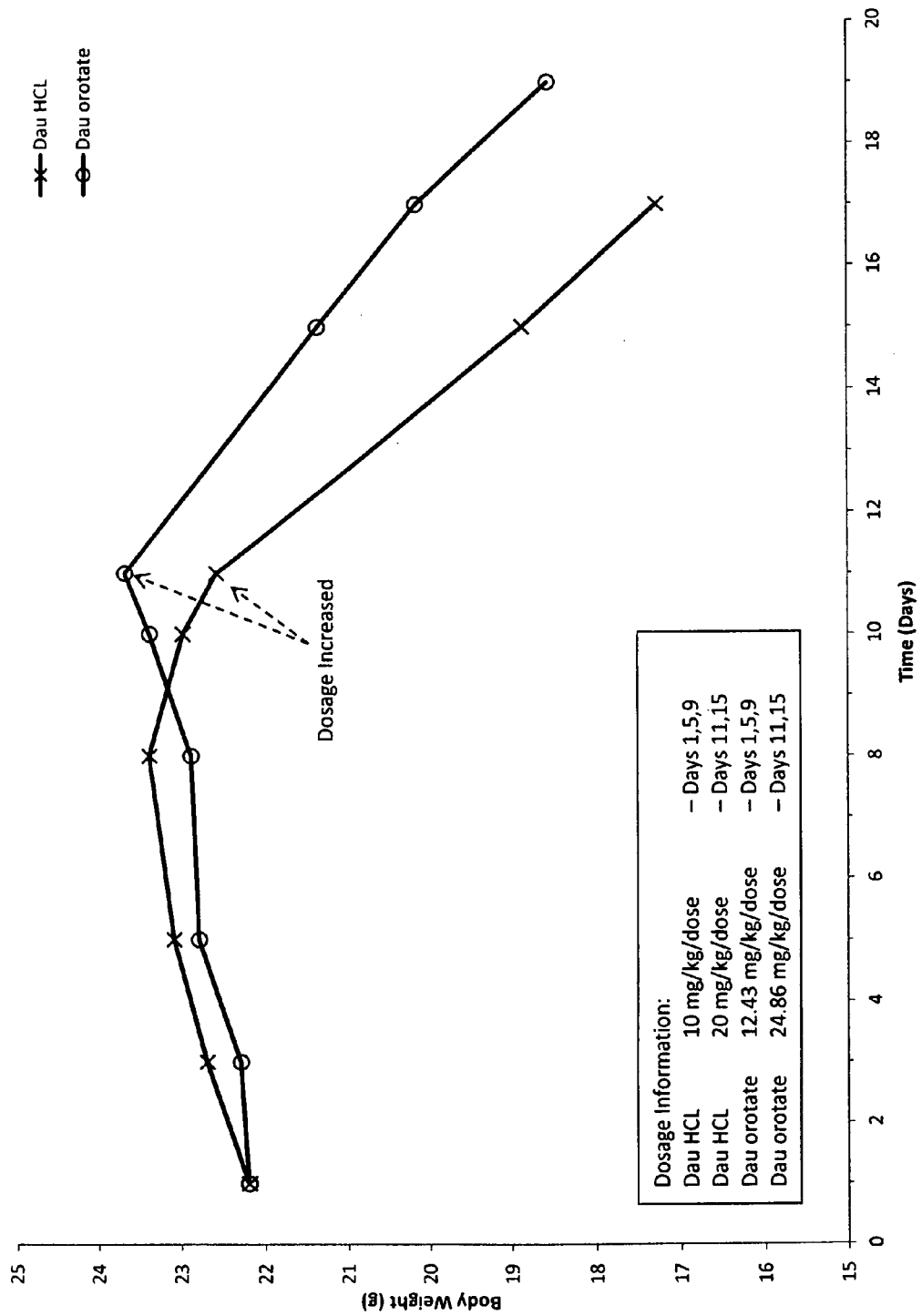
FIG. 4 illustrates the Effect of daunorubicin orotate on body weight compared to Daunorubicin Hydrochloride.

Comparison of Tolerability of Daunorubicin hydrochloride and Daunorubicin Orotate when Administered Intravenously to Athymic Nude Mice The purpose of the experiment was to compare the tolerance of female athymic NCr-nu/nu mice to the intravenous (IV) treatment with daunorubicin HCl and daunorubicin orotate. Female six-week-old athymic NCr-nu/nu mice were purchased from Charles River Laboratories (Wilmington, Mass.) and acclimated in the laboratories for six days prior to experimentation. The study consisted of two groups of five mice per group. All treatments were administered intravenously (IV) and were initiated on Day 1. Animals in Group 1 were treated with daunorubicin HCl at a dose of 10 mg/kg/injection once every four days for a total of three injections (Q4D×3, Days 1, 5, and 9) followed by two injections at a dose of 20 mg/kg/injection given four days apart (Q4D×2, Days 11 and 15). Animals in Group 2 were treated with daunorubicin orotate at a dose of 12.43 mg/kg/injection on a Q4D×3 schedule (on Days 1, 5, and 9) followed by two injections at a dose of 24.86 mg/kg/injection given on a Q4D×2 schedule (on Days 11 and 15). Daunorubicin orotate was tested at the equivalent daunorubicin HCl doses (based on MW of daunorubicin orotate of 701 and MW of daunorubicin HCl of 564). Daunorubicin HCl was formulated on each day of treatment in saline by vortexing. Daunorubicin orotate was formulated on each day of treatment in saline by vortexing and additional sonicating of the 2.486 mg/mL solution for 15 sec. Saline (physiological saline solution, for animal use only, sterile—preservative free) was purchased from Nova-Teck, Inc. Both dosing solutions were kept at room temperature after formulation and were administered within approximately 30 minutes of formulation. Daunorubicin HCl and daunorubicin orotate were administered to mice by exact individual animal's body weight on each day of treatment, with the treatment volume being 0.1 mL/10 g body weight. Body Weights—Animals were checked and mortality was recorded once daily. The animals were weighed three times a week starting on Day 1. Group mean body weights are presented in FIG. 4. Days of deaths and twenty-one-day survival were evaluated. SigmaStat version 3.5 statistical software was used to compare statistically the body weights. The individual animals' body weights were used as endpoints in a t-test. The difference between the groups was considered to be significant if the P value was equal to or less than 0.05.

Results—The treatment with daunorubicin HCl (Group 1) at a dose of 10 mg/kg/injection on Days 1, 5, and 9 was tolerated without deaths. Animals gained weight until Day 11. Thus, the dose of daunorubicin HCl of 10 mg/kg/injection when administered on a Q4D×3 schedule was well tolerated. In order to observe toxicity a dose of 20 mg/kg/injection of daunorubicin HCl, believed to be above the tolerated dose when administered on a Q4D×3 schedule, was administered to mice starting on Day 11. The treatments with daunorubicin HCl at a dose of 20 mg/kg/injection on Days 11 and 15 resulted in a mean body weight loss of 22% (4.9 g), observed on Day 17. Therefore, Maximum Tolerated Dose (MTD) (20% body weight loss) was exceeded. MTD is defined as the dose which does not result in death or produces no more than 20% mean body weight loss.

The treatment with daunorubicin orotate (Group 2) at a dose of 12.43 mg/kg/injection on Days 1, 5, and 9 was tolerated without deaths. Animals gained weight until Day 11. Thus, the dose of daunorubicin orotate of 12.43 mg/kg/injection when administered on a Q4D×3 schedule was well tolerated. In order to observe toxicity a dose of 24.86 mg/kg/injection of daunorubicin orotate was administered to mice starting on Day 11. The treatments with daunorubicin orotate at a dose of 24.86 mg/kg/injection on Days 11 and 15 resulted in a mean body weight loss of 9% (2.0 g), observed on Day 17. Hence daunorubicin orotate was tolerated much better (only 9% body weight loss) compared to daunorubicin hydrochloride (22% body weight loss) at the higher equivalent dose. Body weights on Day 17 in the group treated with daunorubicin hydrochloride were statistically different (smaller) when compared to body weights of mice in the group treated with daunorubicin orotate (P<0.001). This translates to an improvement in tolerance to daunorubicin of 13% as measured by % changes in body weight in daunorubicin given as orotate salt compared to daunorubicin given as chloride in animals. Such an effect in pediatric, adult and geriatric cancer patients will be greatly welcome and highly needed because it can mean life instead of death and better quality of life. Change in mean body weights over the course of the experiment in both groups is presented graphically in FIG. 4. The present invention provides a daunorubicin orotate composition and a method of improving the tolerability of daunorubicin in animals, when used as an orotate salt.

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims. Those skilled in the art will recognize, or be able to ascertain using no more than routine experimentation, any equivalents to the specific embodiments of the invention described herein. Such equivalents are intended to be encompassed by the claims.

What is claimed is:

1. A composition comprising daunorubicin orotate, wherein daunorubicin orotate is the only drug in said composition.

2. A compound of the formula:

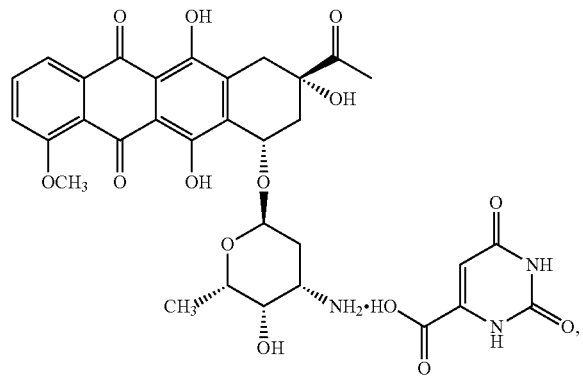

in solid form.

* * * * *